US007060165B2

(12) United States Patent
Brandstater et al.

(10) Patent No.: US 7,060,165 B2
(45) Date of Patent: Jun. 13, 2006

(54) PROCESSES FOR PURIFICATION AND PRODUCTION OF FLUOROCARBONS

(75) Inventors: Stephan M. Brandstater, Indianapolis, IN (US); Mitchel Cohn, West Lafayette, IN (US); Victoria E. Hedrick, Brookston, IN (US); Yuichi Iikubo, West Lafayette, IN (US)

(73) Assignee: PCBU Services, Inc., Wilmington, DE (US)

( * ) Notice: Subject to any disclaimer, the term of this patent is extended or adjusted under 35 U.S.C. 154(b) by 447 days.

(21) Appl. No.: 10/075,560

(22) Filed: Feb. 14, 2002

(65) Prior Publication Data

US 2003/0164283 A1    Sep. 4, 2003

(51) Int. Cl.
*B01D 3/36*    (2006.01)
*B01D 3/40*    (2006.01)
*C07C 17/386*    (2006.01)

(52) U.S. Cl. .......................... 203/29; 203/67; 570/165; 570/178

(58) Field of Classification Search .................. 203/29, 203/50, 67, 70; 570/177, 178, 165
See application file for complete search history.

(56) References Cited

U.S. PATENT DOCUMENTS

| 2,494,064 | A |   | 1/1950  | Simons et al.     |         |
|-----------|---|---|---------|-------------------|---------|
| 5,087,329 | A |   | 2/1992  | Felix             |         |
| 5,453,551 | A |   | 9/1995  | Lacroix et al.    |         |
| 5,679,876 | A |   | 10/1997 | Hub et al.        |         |
| 5,892,137 | A |   | 4/1999  | Bertocchio et al. |         |
| 5,912,392 | A | * | 6/1999  | Vollmueller et al. | 570/165 |
| 5,919,340 | A |   | 7/1999  | Kohno et al.      |         |
| 5,932,775 | A |   | 8/1999  | Lacroix et al.    |         |
| 6,025,532 | A |   | 2/2000  | Sage et al.       |         |
| 6,039,845 | A |   | 3/2000  | Bertocchio et al. |         |
| 6,281,395 | B1| * | 8/2001  | Nappa et al.      | 570/165 |
| 6,333,440 | B1| * | 12/2001 | Malikarjuna       | 570/178 |

FOREIGN PATENT DOCUMENTS

| EP | 0 366 797 A1 |   | 10/1989 |
|----|--------------|---|---------|
| EP | 0 612 709    | * | 8/1994  |
| EP | 0 626 362    | * | 11/1994 |
| EP | 0 669 302 A1 |   | 8/1995  |
| EP | 0 669 392 B1 |   | 12/1995 |
| EP | 0 626 362 B1 |   | 6/1996  |
| EP | 1 153 907    | * | 11/2001 |
| FR | 97 00053     |   | 7/1998  |
| GB | 902 590 A    |   | 8/1962  |
| GB | 1013991 A    |   | 12/1965 |
| JP | 8-3082       |   | 1/1996  |
| JP | 8-143486     |   | 6/1996  |
| WO | 94/19301     | * | 9/1994  |
| WO | 94/25419     | * | 11/1994 |
| WO | 95/21147     | * | 8/1995  |
| WO | 95/21148     | * | 8/1995  |
| WO | WO 95/21147  |   | 8/1995  |
| WO | WO 95/21148  |   | 8/1995  |
| WO | 95/27689     | * | 10/1995 |
| WO | WO 95/27689  |   | 10/1995 |
| WO | WO 96/06063  |   | 2/1996  |
| WO | 96/07627     | * | 3/1996  |
| WO | WO 96/07627  |   | 3/1996  |
| WO | 96/24569     | * | 8/1996  |
| WO | WO 96/24569  |   | 8/1996  |
| WO | 98/15511     | * | 4/1998  |
| WO | WO 98/15511  |   | 4/1998  |
| WO | WO 98/52889  |   | 11/1998 |
| WO | WO 99/07660  |   | 2/1999  |
| WO | WO 99/10302  |   | 3/1999  |
| WO | 99/10302     | * | 4/1999  |

OTHER PUBLICATIONS

Written Opinion from the International Preliminary Examining Authority for PCT/US 03/03962.
International Preliminary Examination Report for PCT/US 03/03962.
International Search Report for PCT/US03/03966.

* cited by examiner

*Primary Examiner*—Virginia Manoharan
(74) *Attorney, Agent, or Firm*—Wells St. John P.S.

(57) ABSTRACT

The present invention involves processes that utilize an olefinic compound, in particular, hexafluoropropene (HFP) or chlorotrifluoroethene (CFC-1113) as extracting agents in the purification of pentafluoroethane (HFC-125). These processes can utilize recovered HFP as a precursor for the production of heptafluoropropane (HFC-227) or other derivatives.

27 Claims, No Drawings

PROCESSES FOR PURIFICATION AND PRODUCTION OF FLUOROCARBONS

FIELD OF INVENTION

The present invention relates to processes for separating pentafluoroethane ($CHF_2-CF_3$, HFC-125) from a mixture comprising HFC-125 and chloropentafluoroethane ($CF_3-CClF_2$, CFC-115). The present invention further relates to the production of heptafluoropropane ($CF_3CHFCF_3$ or $CF_3CF_2CHF_2$, HFC-227ea or HFC-227ca, collectively HFC-227).

BACKGROUND OF THE INVENTION

In the recent years, there has been an increasing concern about global warming. As a result, several chlorofluorocarbons (CFC's) that are known to have an adverse environmental impact have been removed from the marketplace. In their place, new compounds have been introduced as flooding agents, streaming agents, blowing agents, propellants, and refrigerants. However, some of these new compounds do not meet environmental safety requirements. Consequently, there is a constant need to develop fluorocarbon compounds, especially hydrofluorocarbons, which have no chlorine. Two hydrofluorocarbons that are known to have desirable properties are pentafluoroethane (HFC-125) and heptafluoropropane (HFC-227).

HFC-125 is a valuable hydrofluorocarbon (HFC) that is especially useful as a refrigerant, blowing agent, propellant, or fire-extinguishing agent. HFC-125 can be prepared by a multi-step process starting with fluorination of tetrachloroethene ($C_2Cl_4$). The end products of the multi-step process include a mixture containing HFC-125, chloropentafluoroethane (CFC-115), and small amounts of other fluorinated compounds.

HFC-227 is another valuable hydrofluorocarbon. One known starting material for the production of HFC-227 is hexafluoropropene ($CF_3CF=CF_2$, HFP). HFP can be hydrofluorinated with hydrogen fluoride (HF) in the presence of a suitable catalyst to form HFC-227 and other byproducts. Typically, in the final step of HFC-227 purification, these byproducts are separated out by simple distillation.

CFC-115 is an undesirable compound because it contains chlorine, and, as a result, its use is highly regulated. Thus, in the production of HFC-125 for commercial use, it is necessary to separate HFC-125 from CFC-115. Unfortunately, the mixture of HFC-125 and CFC-115 forms a near-azeotrope. At high concentrations of HFC-125, the relative volatility of HFC-125 to CFC-115 is close to 1.0, making recovery of pure HFC-125 from a mixture of HFC-125 and CFC-115 by simple distillation difficult.

An azeotrope is a liquid mixture that exhibits a maximum or minimum boiling point relative to the boiling points of its components. An azeotrope is homogeneous if only one liquid phase is present. An azeotrope is heterogeneous if more than one liquid phase is present. Regardless, a characteristic of azeotropes is that the bulk liquid composition is identical to the vapor composition in equilibrium therewith, and distillation of the azeotropic mixture is ineffective as a separation technique. For the purposes of this discussion, a near-azeotrope means a composition which behaves like an azeotrope (i.e., has constant-boiling characteristics or a tendency not to fractionate upon boiling or evaporation). Thus, the composition of the vapor formed during boiling or evaporation of such compositions is the same as or substantially the same as the original liquid composition. Hence, during boiling or evaporation, the liquid composition, if it changes at all, changes only to a minimal or negligible extent. This is to be contrasted with non-azeotrope compositions in which during boiling or evaporation, the liquid composition changes to a substantial degree.

Accordingly, the essential features of an azeotrope or a near-azeotrope are that at a given pressure, the boiling point of the liquid composition is fixed and that the composition of the vapor above the boiling composition is essentially that of the boiling liquid composition (i.e., no fractionation of the components of the liquid composition takes place). It is recognized in the art that both the boiling point and the weight percentages of each component of the azeotropic composition may change when the azeotrope or near-azeotrope liquid composition is subjected to boiling at different pressures. Thus, an azeotrope or a near-azeotrope may be defined in terms of the unique relationship that exists among components or in terms of the compositional ranges of the components or in terms of exact weight percentages of each component of the composition characterized by a fixed boiling point at a specified pressure. It is also recognized in the art that various azeotropic compositions including their boiling points at particular pressures may be calculated (see, e.g., W. Schotte, Ind. Eng. Chem. Process Des. Dev. 1980, 19, pp 432–439). Experimental identification of azeotropic compositions involving the same components may be used to confirm the accuracy of such calculations and/or to modify the calculations for azeotropic compositions at the same or other temperatures and pressures.

It is known that pure HFC-125 as a near-azeotropic mixture with CFC-115 can be recovered by a process of extractive distillation. In this process, a suitable extracting agent that changes the relative volatility of a component or the azeotrope is used. Examples of extracting agents used in the purification of HFC-125 are disclosed in U.S. Pat. Nos. 5,087,329 and 5,928,479.

Extractive distillation processes for the purification of HFC-125 usually include a step of separating the extracting agent from either HFC-125 or CFC-115 subsequent to the completion of the extractive distillation. This additional separation process may add to the cost of HFC-125 production even though the extracting agent may be reused.

SUMMARY OF INVENTION

The present invention provides processes for the production of halogenated hydrocarbons either alone or in combination with the synthesis of olefinic derivatives. In one embodiment of the present invention, at least one halogenated hydrocarbon is purified from a near-azeotropic mixture comprising at least one halogenated hydrocarbon and at least one halocarbon by extractive distillation using an olefinic extracting agent. In this particular embodiment, the olefinic extracting agent is converted into a derivative compound.

In another embodiment of the present invention, HFC-125 is purified from a mixture containing CFC-115 by extractive distillation, using hexafluoropropene (HFP) or chlorotrifluoroethene ($CClF=CF_2$, CFC-1113) as an extracting agent. One feature of this particular embodiment is that the extracting agent can be recovered and reused in the purification of HFC-125 as set forth herein. In an alternative embodiment, the recovered extracting agent can be used as a starting material for the production of fluorocarbons like HFC-227.

In a specific embodiment of the present invention, the process of recovering HFC-125 comprises the steps of: (a)

providing a first mixture comprising HFC-125 and CFC-115, (b) distilling the first mixture in the presence of hexafluoropropene (HFP) to separate HFC-125 from a second mixture comprising HFP and CFC-115. The distilling process may be extractive distillation, in which HFP is an extracting agent.

According to another embodiment of the invention, the process may further include the steps of: (c) recovering HFC-125 as an overhead product and (d) recovering the second mixture as a bottom product.

According to a further embodiment, the process may further include the step of: (e) purifying HFP from the second mixture to produce a third mixture comprising CFC-115 and the step of (f) recovering HFP. Optionally, the process may include the step of re-using the recovered HFP as an extracting agent, as described herein.

Another embodiment of the present invention is directed to a process comprising the steps of: (a)–(d), as described, and the steps of: (g) adding HF to the second mixture to form a fourth mixture, (h) converting HFP in the fourth mixture by hydrofluorination in the presence of a suitable catalyst to HFC-227 to produce a fifth mixture, (i) separating the fifth mixture into HFC-227 and a sixth mixture comprising CFC-115, and (j) recovering HFC-227.

A further embodiment of the present invention is directed to a process comprising the steps of: (a)–(f), as described, and the steps of: (k) adding HF to the recovered HFP, (l) converting the recovered HFP by hydrofluorination to HFC-227 in the presence of a suitable catalyst to produce a seventh mixture, (m) separating the seventh mixture into HFC-227 and byproducts, and (n) recovering HFC-227.

In another embodiment, the process comprises the steps of: (a)–(f), as described, and the step of converting HFP to at least one HFP derivative or a fluoropolymer.

In an alternative embodiment of the present invention, the process comprises the steps of: (o) providing a first mixture comprising HFC-125 and CFC-115, (p) distilling the first mixture in the presence of CFC-1113 to separate HFC-125 from an eighth mixture comprising CFC-1113 and CFC-115, (q) recovering HFC-125 as an overhead product, and (r) recovering the eighth mixture as a bottom product. The distilling process may be extractive distillation, in which HFP is an extracting agent.

In still another embodiment, the process comprises the steps of (o)–(r) and the steps of: (s) adding HF to the eighth mixture to produce a ninth mixture, (t) converting CFC-1113 in the ninth mixture in the presence of a suitable catalyst to a fluoroethane to make a tenth mixture, and recycling the tenth mixture to a hydrofluorocarbon production process. In one embodiment, the fluoroethane is 1-chloro-1,2,2,2-tetrafluoroethane ($CHClFCF_3$, HCFC-124).

The above and other embodiments, aspects, alternatives and advantages of the present invention will become more apparent from the following detailed description of the present invention taken in conjunction with the examples.

DETAILED DESCRIPTION OF THE INVENTION

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications as would be conveyed to one skilled in the art to which the invention relates.

The present invention overcomes the shortcomings of the prior art by providing innovative processes for producing hydrofluorocarbons by separating mixtures of near-azeotrope halogenated hydrocarbons with extracting agents and subsequently converting the extracting agent to a derivative compound that can be separated from at least one of the halogenated hydrocarbons from the near-azeotropic mixture.

In one embodiment, the present invention involves the use of an extracting agent, namely HFP, that can be used to purify HFC-125 from a mixture comprising HFC-125 and CFC-115. The mixture may contain mostly HFC-125 and only minute amounts of CFC-115 and other fluorocarbon byproducts. HFP is an important monomer used to produce organic fluorine materials and is readily available in the marketplace.

The use of HFP as an extracting agent for the separation of alkanes has never been described in the prior art. It is commonly known that similar compounds are attracted to each other. Thus, typically, in order to separate chlorine containing alkanes from non-chlorine containing alkanes, another chlorine containing alkane is used as an extracting agent. As an alkene, HFP is structurally different from the alkanes disclosed as extracting agents in the U.S. Pat. No. 5,087,329. This structural difference in combination with the fact that HFP contains no chlorine made its usefulness as an extracting agent for separating HFC-125 from CFC-115 unexpected. The use of HFP and fluorinated alkenes as extracting agents is demonstrated below in non-limiting Example 1.

EXAMPLE 1

Screening of Extracting Agents for Vapor Phase Separation of HFC-125 and CFC-115

A 50 cc stainless steel sample cylinder fitted with a pressure gauge and valve with a septum port was chilled to −78° C. and a known amount of HFC-125 and CFC-115 was charged to the cylinder. This mixture was shaken and allowed to warm to ambient temperature and the vapor phase was sampled for subsequent analysis by gas chromatography (GC).

The cylinder was then re-cooled to −78° C. and a desired amount of the chosen extraction solvent was added to the vessel. The mixture was then allowed to warm to ambient temperature, at which time, it was shaken and allowed to equilibrate for 3 to 12 hours before it was re-sampled for GC analysis.

All GC data of this and the following examples were taken by sampling a collection or storage vessel or the appropriate sample port with a 50 to 250 μL airtight syringe fitted with an on/off valve. This collected sample was injected on either an HP-5890 or 5890II GC equipped with a Varian plot fused silica column (30 m×0.32 mm ID). All analyses were done using a time-temperature program which had an initial temperature and time of 70° C. and 15 min followed by a ramp to 140° C. at a rate of 15° C./min and a final time of 20 min. Selection of column type, sample size and analysis conditions are well known to those skilled in the art of GC. All amounts noted were based on area percent. To verify the identity of each compound, analyses were performed using mass spectrometry.

TABLE I is a result of the GC analyses of vapor phase content of HFC-125 and CFC-115 in the starting mixture and the mixture with extracting agent that absorbs CFC-115. As shown in TABLE I, relative volatility of CFC-115 changed with the addition of different solvents. The volatility of CFC-115 was relatively low with the addition of the CFC-solvents, like 1,1,2-trichloro-1,2,2-trifluoroethane ($CCl_2FCClF_2$, CFC-113) and 1,2-dichloro-1,1,2,2-tetrafluoroethane ($CClF_2CF_2Cl$, CFC-114). Thus, these solvents, CFC-113 and CFC-114, performed well in the separation of CFC-115 from HFC-125, as shown by the increase in the percent of HFC-125 or the decrease in the percent of CFC-115 in the vapor phase. As expected, the similar compounds like dichlorohexafluoropropane ($C_3F_6Cl_2$, CFC-216) and chloroheptafluoropropane ($C_3F_7Cl$, CFC-217) also exhibited good extracting ability for CFC-115. However, being chlorofluorocarbons, these compounds are not desirable extracting agents because they are highly regulated suspect ozone depleting compounds.

The efficiency of the fluoro-olefins, namely CFC-1113, HFP, HFC-1243zf ($CF_3CH=CH_2$, TFP), and HFC-1225zc ($CF_3CH=CF_2$, PFP) varied. CFC-1113 and HFP demonstrated a surprising ability to extract CFC-115 from HFC-125. However, since HFP contains no chlorine, it may be more useful as an extracting agent.

In contrast to HFP and CFC-1113, the olefins HFC-1243zf and HFC-1225zc had little or no extractive power. In addition, chloroform ($CHCl_3$) did not appear to be an effective extracting agent for the separation of CFC-115.

produce HCFC-124. In these embodiments, the relative volatility of the extracting agent derivative is sufficiently disparate from CFC-115 that the derivative can be readily separated by known chemical separation techniques such as distillation. Further, CFC-1113 may also be converted to HFC-125 or a mixture of HFC-125 and HCFC-124, in which case it may be recycled to the HFC-125/CFC-115 purification process to produce more HFC-125.

These types of hydrohalogenation reactions are commonly performed in the presence of a catalyst. Suitable gas phase catalysts include activated carbon, chromium oxide, nickel, copper, iron, or aluminum oxide. Suitable liquid phase catalysts include antimony chloride, molybdenum, and tantalum. It is contemplated that other compounds and synthetic schemes can be used to derivatize the extracting agent. The resulting compound may be recovered or recycled back to the separation process.

According to a specific embodiment of the present invention, a process for separating HHFC-125 from CFC-115 is provided. The process includes a step of (a) providing a first mixture comprising HFC-125 and CFC-115. The first mixture may be derived from a hydrofluorination reaction of tetrachloroethene, or other similar processes. The first mixture may also contain small amounts of other hydrofluorination byproducts such as 1,1,2-trichloro-1,2,2-trifluoroethane (CFC-113), 1,2-dichloro-1,1,2,2-tetrafluoroethane (CFC-114), 2,2-dichloro-1,1,1-trifluoroethane (HCFC-123),

TABLE I

GC Analysis of the vapor phase content of HFC-125 and CFC-115 in starting mixture and mixture with extracting agent that absorbs CFC-115

| Extracting agent | % HFC-125 | | | % CFC-115 | | Relative Volatility of CFC-115 |
|---|---|---|---|---|---|---|
| | At start | Extracting agent added | Change | At start | Extracting agent added | |
| $CHCl_3$ | 98.28 | 98.28 | 0.00 | 1.72 | 1.72 | 1.00 |
| HFC-1243zf | 99.02 | 99.04 | 0.02 | 0.98 | 0.96 | 0.98 |
| HFC-1225zc | 99.14 | 99.17 | 0.03 | 0.86 | 0.83 | 0.96 |
| $C_2Cl_4$ | 98.28 | 98.49 | 0.21 | 1.72 | 1.51 | 0.88 |
| CFC-217 | 98.28 | 98.52 | 0.24 | 1.72 | 1.48 | 0.86 |
| CFC-216 | 98.28 | 98.54 | 0.26 | 1.72 | 1.46 | 0.85 |
| $CCl_4$ | 98.28 | 98.54 | 0.26 | 1.72 | 1.46 | 0.85 |
| HFP | 99.02 | 99.18 | 0.16 | 0.98 | 0.82 | 0.84 |
| CFC-1113 | 99.14 | 99.31 | 0.17 | 0.86 | 0.69 | 0.80 |
| CFC-114 | 98.28 | 98.78 | 0.50 | 1.72 | 1.22 | 0.71 |
| CFC-113 | 98.28 | 98.82 | 0.54 | 1.72 | 1.18 | 0.69 |

In certain embodiments, the present invention involves utilizing olefinic extracting agents in two different ways. First, the olefinic extracting agent can be used to purify HFC-125 from a mixture comprising HFC-125 and CFC-115. Relatively pure HFC-125 is recovered as the overhead product, while the majority of the olefinic extracting agent is recovered as a mixture with CFC-115 as a bottom product. In one embodiment, the olefinic extracting agent is HFP. In another embodiment, the olefinic extracting agent is CFC-1113.

Second, after it is used as an extracting agent, the olefinic extracting agent can be recovered and used as a precursor for the production of extracting agent derivatives or fluoropolymers. As an olefin, the recovered extracting agent lends itself to hydrohalogenation by addition across the double bond.

In one embodiment, HF is added across the double bond of HFP to produce HFC-227. In another embodiment, HF may be added across the double bond of CFC-1113 to or hexafluoroethane (FC-116). The percent concentration of HFC-125 and CFC-115 in the first mixture may vary. The first mixture may contain more than 90% of HFC-125.

The first mixture is fed to a fractionation column. In this specific embodiment of the invention, the process further comprises the step of (b) distilling the first mixture in the presence of HFP to separate HFC-125 from a second mixture comprising HFP and CFC-115. During this step, HFP is added to the upper section of the fractionation column. As much as about 50% HFP by weight of HFC-125 may be used, although more than 50% HFP by weight of HFC-125 may be used if desired. However, preferably 20% HFP by weight of HFC-125 is used.

The distillation is performed at a condition that allows HFC-125 to pass substantially free of CFC-115 to the top of the column where it is condensed. Some of the HFC-125 may be returned as reflux. Simultaneously, HFP and CFC-115 pass to the bottom of the column as a second mixture.

It is possible for the second mixture to also contain residual HFC-125 and other compounds that are present in the first mixture. Finally, in a particular embodiment, the process includes the steps of (c) recovering HFC-125 as an overhead product and (d) recovering the second mixture as a bottom product. One embodiment of this process is demonstrated below in non-limiting Example 2.

EXAMPLE 2

Vapor Phase Separation of HFC-125 from CFC-115 Using HFP as an Extracting Agent

This procedure demonstrates the effective removal of CFC-115 from streams of the first mixture comprising HFC-125 and CFC-115, by the use of HFP as an extracting agent.

The apparatus used was a 92 in. packed, schedule 40, carbon steel distillation column fitted with a reboiler, overhead condenser, overhead reflux loop, timed take-off valves, and multiple feed points. This evacuated column was charged with 584 g of the first mixture comprising 97.928% of HFC-125 and 2.073% of CFC-115, by weight. This mixture was allowed to equilibrate at a reflux ranging from 14 to 29 cc/min. HFP was then fed into the column at an average rate of 1.98 g/min, while taking off CFC-115 and HFP at a rate of 1.75 g/min as the bottom product from the reboiler.

The operation was continued over 2348 minutes. The total amount of HFP added was 4438 g. During this time, the relative ratio of HFC-125 to CFC-115 in the overhead of the column increased from 87 to 8194 (TABLE II). This ratio represents approximately 121 ppm (0.0121% GC-Area) of CFC-115 remaining in the overhead fraction (TABLE II).

The recovery from the reboiler shows that most of the HFP was recaptured in the reboiler or the bottom fraction. This bottom fraction also contained CFC-115 and residual HFC-125 (TABLE II).

At the end of the operation, the initial charge, including the amount of the first mixture and the total amount of HFP used, is compared to the final recovery in both the reboiler and the overhead fractions. The results show a total mass balance accountability of 96.6%.

In another embodiment of the present invention, the process further includes the step of (e) purifying HFP in the second mixture to produce relatively pure HFP and a third mixture comprising CFC-115 and the step of (f) recovering HFP. The third mixture may include residual HFP and HFC-125. In addition, the third mixture may also include small amounts of byproducts, as indicated above. The recovered HFP from this purification step may contain a minute amount of CFC-115 and other byproducts. The purification step may involve any appropriate technique including distillation. The purification of HFP by simple distillation is demonstrated below in non-limiting Example 3.

EXAMPLE 3

Purification of HFP

To demonstrate this process, 507 grams of a mixture containing 90.17% of HFP, 9.798% of HFC-125, and 0.025% of CFC-115 (see TABLE III) was charged to an apparatus consisting of a 92 in. packed, schedule 40, carbon steel distillation column fitted with a reboiler, overhead condenser, and overhead reflux loop. This mixture was allowed to equilibrate with a steady reflux for 224 minutes. The distillation was run at a pressure of about 122–123 psig. The boiler temperature was set at about 31.4° C., and the overhead temperature was set at about 27° C. The overhead and reboiler compositions were checked by GC analysis. The column was then equilibrated for another 100 minutes to obtain further homogeneity of the HFP in the reboiler of the column (see TABLE III). This demonstrates that the longer the distillation was run, the higher purity of HFP was obtained. This level of purity is acceptable for recycle to the HFC-125 extractive distillation system or to be used as a raw material in subsequent downstream reactions.

TABLE II

Extractive distillation using HFP as an extracting agent to separate HFC-125 from CFC-115

| | | Column Overhead | | | Column Reboiler | | |
|---|---|---|---|---|---|---|---|
| Time (min) | HFP Feed (g) | HFC-125 (% GC-Area) | CFC-115 (% GC-Area) | Relative ratio of HCF-125 to CFC-115 | HFC-125 (% GC-Area) | CFC-115 (% GC-Area) | HFP (% GC-Area) |
| 5 | 9 | 98.8076 | 1.1361 | 87 | 96.5055 | 2.4569 | 0.3507 |
| 71 | 134 | 98.3079 | 0.8889 | 111 | | | |
| 267 | 505 | 99.4534 | 0.4757 | 209 | 1.9543 | 0.2929 | 97.7323 |
| 515 | 973 | 99.0789 | 0.3670 | 270 | | | |
| 764 | 1444 | 99.4312 | 0.4172 | 238 | 0.0264 | 0.0241 | 99.9367 |
| 954 | 1803 | 98.7882 | 0.1890 | 523 | | | |
| 1158 | 2189 | 99.7811 | 0.1492 | 669 | 0.0359 | 0.0055 | 99.9473 |
| 1357 | 2565 | 99.0762 | 0.0797 | 1243 | | | |
| 1573 | 2973 | 99.8564 | 0.0653 | 1529 | 0.0301 | 0.0013 | 99.9531 |
| 1918 | 3625 | 99.2493 | 0.0286 | 3465 | | | |
| 2102 | 3973 | 99.8944 | 0.0303 | 3297 | 0.0265 | 0.0035 | 99.9554 |
| 2234 | 4222 | 99.4617 | 0.0268 | 3711 | | | |
| 2348 | 4438 | 99.3941 | 0.0121 | 8194 | 0.0356 | 0.0023 | 99.9620 |

TABLE III

Separation of HFP from HFC-125 and CFC-115 by distillation

| | Equilibrium Time (min) | % GC-Area | | |
|---|---|---|---|---|
| | | HFC-125 | CFC-115 | HFP |
| Starting Mixture | 0 | 9.798 | 0.025 | 90.174 |
| Overhead | 244 | 18.379 | 0.035 | 81.586 |
| Reboiler | 244 | 2.769 | 0.014 | 97.209 |
| Overhead | 344 | 18.491 | 0.034 | 81.460 |
| Reboiler | 344 | 1.049 | 0.013 | 98.934 |

The recovered HFP may be recycled to be used as an extracting agent in the process of recovering HFC-125 described herein. In another embodiment, the recovered HFP may be converted to at least one of HFP derivatives such as HFC-227, or polymers such as elastomers, plastomers, resins, and fluoropolymers.

Another specific embodiment of the present invention comprises the steps of (a)–(d), as described herein, and the further steps of (g) adding HF to the second mixture to form a fourth mixture and (h) converting HFP in the fourth mixture to HFC-227 by hydrofluorination to form a fifth mixture. The benefits of this embodiment are demonstrated by way of non-limiting Example 4 below.

EXAMPLE 4

Converting HFP to HFC-227 by Selective Hydrofluorination in the Presence of HFC-125 and CFC-115

A 34 cc alloy-600 reactor tube was charged with 13.1 g of activated carbon catalyst and dried overnight at 155° C. with a nitrogen purge. The reaction outlet was configured with an aqueous scrubber filled with dilute caustic followed by a Drierite tube, GC sampling port, and optional cold trap. Three different mixtures were used as the starting material in the reaction runs (# 1–3). Each mixture comprises HFP and minute amounts of CFC-115 and HFC-125 (see TABLE IV). In the # 4, relatively pure HFP was used as the starting material for comparison.

TABLE IV

Composition (% GC) of starting material for four reaction runs of fluorination of HFP to HFC-227

| | % GC-Area | | |
|---|---|---|---|
| Run# | HFP | HFC-125 | CFC-115 |
| 1 | 99.960 | 0.024 | 0.009 |
| 2 | 99.396 | 0.540 | 0.055 |
| 3 | 86.979 | 12.750 | 0.419 |
| 4 | 99.991 | — | — |

Specific conditions of each fluorination reaction run using the materials shown in TABLE IV are shown in TABLE V. For each run, the starting material was supplied to the reactor tube described above. HF was first added to the reactor tube at a rate of about 70 to 74 cc/min. The flow rate of the starting material was about 47 to 60 cc/min. The ratio of HF to HFP ranged from 1.28 to 1.60. The fluorination reaction was run at a temperature of about 200° C. (see TABLE V). The contact time ranged from 9.16 to 10.08 seconds.

TABLE V

Fluorination conditions of four fluorination reaction runs using four starting materials shown in TABLE IV

| | | | Flow rate | | |
|---|---|---|---|---|---|
| Run # | Temp. (° C.) | Contact Time (sec) | HF (cc/min) | Starting Material HFP/115/125 (cc/min) | Molar Ratio HF:HFP |
| 1 | 203 | 9.16 | 72.80 | 55.71 | 1.28 |
| 2 | 205 | 9.58 | 70.00 | 59.90 | 1.29 |
| 3 | 204 | 9.66 | 74.23 | 47.46 | 1.57 |
| 4 | 204 | 10.08 | 73.05 | 43.81* | 1.60 |

*HFP only

The result of each fluorination reaction run shown in TABLE V is reported in TABLE VI. Percent conversion of HFP to HFC-227 ranged from about 92.13 to 97.24, while selectivity ranged from about 85 to about 99%. The amounts of HFC-125 and CFC-115 did not substantially change from what was present in the starting materials (see TABLE IV and VI). Thus, the data in TABLE VI indicate that olefins can be selectively fluorinated without causing any serious side reactions or lowering of conversion while allowing HFC-125 and CFC-115 to pass through the system essentially unchanged.

TABLE VI

The results of the fluorination process based on the conditions shown in TABLE V

| | HFC-227 | | | |
|---|---|---|---|---|
| Run # | Conversion % | Selectivity % | HFC-125 % GC-Area | CFC-115 % GC-Area |
| 1 | 92.13 | 99.27 | 0.0231 | 0.0065 |
| 2 | 95.54 | 98.58 | 0.5617 | 0.0421 |
| 3 | 96.62 | 85.08 | 13.1312 | 0.4361 |
| 4 | 97.24 | 99.06 | — | — |

In accordance with another embodiment of the present invention, a process includes the steps of (a)–(d), (g)–(h), and the step (i) separating the fifth mixture into HFC-227 and a sixth mixture comprising CFC-115. The sixth mixture may further comprise HFC-125 and other flourination byproducts. The separation can be performed by distillation. Finally, this specific embodiment further includes the step of (j) recovering relatively pure HFC-227. This embodiment is demonstrated below by way of non-limiting Example 5.

EXAMPLE 5

Separation of HFC-227 from HFC-125 and CFC-115

A mixture containing mainly HFC-227 (57.24%), HFC-125 (29.44%), and CFC-115 (13.32%) was used as the starting material to demonstrate the process of HFC-227 separation. An evacuated apparatus consisting of a 92 in. packed, schedule 40, carbon steel distillation column fitted with a reboiler, overhead condenser, and overhead reflux loop was charged with 719 grams of the above described mixture. This mixture was allowed to equilibrate at a reflux ranging from 1.86 to 2.46 cc/min over a 1417 minute time period. The overhead product and the bottom product were collected at three different distillation conditions (see TABLE VII). The content of both the overhead and the bottom products was determined by GC. The results shown in TABLE VII indicate that the majority of HFC-227 was separated in the bottom fraction while HFC-125 and CFC-115 were removed as distillates. When the reboiler temperature was increased from 28.2° C. to 55.3° C. and the vapor pressure was raised from 132 psig to 143 psig, the reflux increased from 1.85 cc/min to 2.46 cc/min, and a significant increase in purity of the HFC-227 in the bottom fraction was observed. Essentially pure HFC-227 (99.92%) could be recovered under one of the conditions tested (144 psig, reboiler temperature 54.8° C., overhead temperature 21.9° C., reflux 2.46 cc/min), while only a small amount of HFC-227 was removed in the overhead fraction. The levels of HFC-227 purity recovered were acceptable for commercial use. The resulting CFC-115 and HFC-125 can either be destroyed, recycled or reacted to form other desirable and useful materials.

TABLE VII

Separation of HFC-227 at three different distillation conditions

| | | % GC-Area | | |
|---|---|---|---|---|
| Condition | Starting Mixture | HFC-227 57.24 | HFC-125 29.44 | CFC-115 13.32 |
| A[a] | Overhead | 32.68 | 47.93 | 19.39 |
| | Reboiler | 97.98 | 0.57 | 1.45 |
| B[b] | Overhead | 5.79 | 73.59 | 20.59 |
| | Reboiler | 99.78 | 0.098 | 0.12 |
| C[c] | Overhead | 3.77 | 74.31 | 21.91 |
| | Reboiler | 99.92 | 0.065 | 0.012 |

[a]132 psig, reboiler temperature 28.2° C., overhead temperature 21.5° C., reflux 1.85 cc/min
[b]143 psig, reboiler temperature 55.3° C., overhead temperature 21.6° C., reflux 2.46 cc/min
[c]144 psig, reboiler temperature 54.8° C., overhead temperature 21.9° C., reflux 2.46 cc/min A further embodiment of the present invention involves a process which comprises the steps of (a)–(f) and the steps of: (k) adding HF to the purified HFP, (l) converting the purified HFP by hydrofluorination to HFC-227 in the presence of a suitable catalyst to form a seventh mixture, (m) separating the seventh mixture into HFC-227 and fluorination byproducts, and (n) recovering relatively pure HFC-227. An example of converting relatively pure HFP to HFC-227 is demonstrated in TABLES IV–VI (see run #4).

According to one embodiment, the suitable catalyst is active carbon, but other catalysts that have been previously described are contemplated.

Additional objects, advantages, and other novel features of the invention will become apparent to those skilled in the art upon examination of the foregoing or may be learned with practice of the invention. The foregoing description of the embodiments of the invention has been presented for purposes of illustration and description. It is not intended to be exhaustive or to limit the invention to the precise form disclosed. Obvious modifications or variations are possible in the light of the above teachings. Embodiments were chosen and described to provide the best illustrations of the principals of the invention and their practical application, thereby enabling one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A process for recovering pentafluoroethane (HFC-125) comprising the steps of:
    (a) providing a first mixture comprising pentafluoroethane (HFC-125) and chloropentafluoroethane (CFC-115); and
    (b) distilling said first mixture in the presence of hexafluoropropene (HFP) to separate pentafluoroethane (HFC-125) from a second mixture comprising hexafluoropropene (HFP) and chloropentafluoroethane (CFC-115).

2. The process according to claim 1 wherein said distilling step comprises extractive distillation.

3. The process according to claim 1 wherein said hexafluoropropene (HFP) is an extracting agent.

4. The process according to claim 1 further comprising the steps of:
    (c) recovering said pentafluoroethane (HFC-125) as an overhead product; and
    (d) recovering said second mixture as a bottom product.

5. The process according to claim 1 further comprising the step of:
    (e) purifying said hexafluoropropene (HFP) in said second mixture to produce a third mixture comprising said chloropentafluoroethane (CFC-115).

6. The process according to claim 5 further comprising the step of:
    (f) recovering said hexafluoropropene (HFP).

7. The process according to claim 6 further including the step of converting hexafluoropropene (HFP) to at least one hexafluoropropene (HFP) derivative.

8. The process according to claim 6 further including the step of converting hexafluoropropene (HFP) to at least one fluoropolymer.

9. The process according to claim 6 further including the step of recycling said hexafluoropropene (HFP) to a process for recovering pentafluoroethane (HFC-125).

10. The process according to claim 6 further comprising the steps of:
    (k) adding hydrogen fluoride (HF) to said hexafluoropropene (HFP);
    (l) converting said hexafluoropropene (HFP) by hydrofluorination to heptafluoropropane (HFC-227) in the presence of a suitable catalyst to form a seventh mixture; and
    (m) separating said seventh mixture into said heptafluoropropane (HFC-227) and hydrofluorination byproducts.

11. The process of claim 10 further including the step of:
    (n) recovering said heptafluoropropane (HFC-227).

12. The process according to claim 1 further comprising the steps of:
    (g) adding hydrogen fluoride (HF) to said second mixture to produce a fourth mixture;
    (h) converting said hexafluoropropene (HFP) in said fourth mixture by hydrofluorination in the presence of a suitable catalyst to heptafluoropropane (HFC-227) to produce a fifth mixture;
    (i) separating said fifth mixture into said heptafluoropropane (HFC-227) and a sixth mixture comprising said chloropentafluoroethane (CFC-115); and
    (j) recovering said heptafluoropropane (HFC-227).

13. The process according to claim 12 wherein said suitable catalyst contains activated carbon.

14. A process for recovering pentafluoroethane (HFC-125) comprising:
    providing a first mixture comprising pentafluoroethane (HFC-125) and chloropentafluoroethane (CFC-115);
    distilling said first mixture in the presence of chlorotrifluoroethene (CFC-1113) to separate pentafluoroethane (HFC-125) from a second mixture comprising the chlorotrifluoroethene (CFC-1113) and the chloropentafluoroethane (CFC-115);
    recovering said pentafluoroethane (HFC-125) as an overhead product; and
    recovering said second mixture as a bottom product.

15. The process according to claim 14 wherein said distilling comprises extractive distillation.

16. The process according to claim 14 wherein said chlorotrifluoroethene (CFC-1113) is an extracting agent.

17. The process according to claim 14 further comprising providing said second mixture to a process for manufacturing pentafluoroethane (HFC-125).

18. The process according to claim 14 further comprising:
    adding hydrogen fluoride (HF) to said second mixture to produce a third mixture; and
    converting a portion of said chlorotrifluoroethene (CFC-1113) in said third mixture to at least one fluoroethane in the presence of a suitable catalyst to produce a fourth mixture.

19. The process according to claim 18 wherein said fluoroethane comprises 1-chloro-1,2,2,2-tetrafluoroethane (HCFC-124).

20. The process according to claim 18 further comprising separating said at least one fluoroethane from said fourth mixture to form a fifth mixture comprising hydrofluorination byproducts.

21. The process according to claim 18 further comprising providing said fourth mixture to a process for recovering pentafluoroethane (HFC-125).

22. A process for producing halogenated hydrocarbons comprising:
    providing a near-azeotropic mixture having at least one halogenated hydrocarbon and at least one halocarbon;
    distilling said near-azeotropic mixture in the presence of chlorotrifluoroethene (CFC-1113) to separate said at least one halogenated hydrocarbon from a remaining mixture comprising said chlorotrifluoroethene and said at least one halocarbon; and
    converting said chlorotrifluoroethene in said remaining mixture to a derivative compound.

23. The process according to claim 22 wherein said derivative compound is 1-chloro-1,2,2,2-tetrafluoroethane (HCFC-124).

24. The process according to claim 22 further including the step of purifying said derivative compound.

25. The process according to claim 22 wherein said at least one halogenated hydrocarbon is pentafluoroethane (HFC-125).

26. The process according to claim 22 wherein said near-azeotropic mixture comprises chloropentafluoroethane (CFC-115) and pentafluoroethane (HFC-125).

27. The process for producing halogenated hydrocarbons according to claim 22 further comprising the step of recovering said at least one halogenated hydrocarbon.

* * * * *

UNITED STATES PATENT AND TRADEMARK OFFICE
CERTIFICATE OF CORRECTION

| | |
|---|---|
| PATENT NO. | : 7,060,165 B2 |
| APPLICATION NO. | : 10/075560 |
| DATED | : June 13, 2006 |
| INVENTOR(S) | : Stephan M. Brandstater |

It is certified that error appears in the above-identified patent and that said Letters Patent is hereby corrected as shown below:

Col. 9, line 43 –
    Replace "In the # 4,relatively pure HFP was used as the starting"
    With --In the reaction run # 4, relatively pure HFP was used as the starting--

Signed and Sealed this

Seventeenth Day of April, 2007

JON W. DUDAS
*Director of the United States Patent and Trademark Office*